US008114892B2

(12) United States Patent
Kim et al.

(10) Patent No.: US 8,114,892 B2
(45) Date of Patent: Feb. 14, 2012

(54) METHODS AND COMPOSITIONS FOR THE TREATMENT OF PARKINSON'S DISEASE

(75) Inventors: Deog Joong Kim, Rockville, MD (US); Chun Hyung Kim, Lexington, MA (US); Kwang Soo Kim, Lexington, MA (US)

(73) Assignee: The McLean Hospital Corporation, Belmont, MA (US)

( * ) Notice: Subject to any disclaimer, the term of this patent is extended or adjusted under 35 U.S.C. 154(b) by 356 days.

(21) Appl. No.: 12/279,473

(22) PCT Filed: Feb. 15, 2007

(86) PCT No.: PCT/US2007/004172
§ 371 (c)(1),
(2), (4) Date: Jan. 13, 2009

(87) PCT Pub. No.: WO2007/098047
PCT Pub. Date: Aug. 30, 2007

(65) Prior Publication Data
US 2009/0226401 A1    Sep. 10, 2009

Related U.S. Application Data

(60) Provisional application No. 60/743,304, filed on Feb. 16, 2006.

(51) Int. Cl.
*A61K 31/4706* (2006.01)
*A61P 25/16* (2006.01)
*A61P 33/06* (2006.01)

(52) U.S. Cl. ........ 514/311; 514/4.6; 514/17.7; 514/18.2

(58) Field of Classification Search .................... 514/4.6, 514/17.7, 18.2, 311
See application file for complete search history.

(56) References Cited

U.S. PATENT DOCUMENTS

| | | | |
|---|---|---|---|
| 2,474,821 A | 7/1949 | Burckhalter et al. | |
| 3,232,944 A | 2/1966 | Allais et al. | |
| 4,593,101 A * | 6/1986 | Arnaud et al. ................ | 546/153 |
| 4,806,537 A | 2/1989 | Roberts | |
| 4,831,033 A | 5/1989 | Roberts | |
| 4,963,565 A | 10/1990 | Gangadharam | |
| 5,430,039 A | 7/1995 | Roberts-Lewis et al. | |
| 6,187,756 B1 | 2/2001 | Lee et al. | |
| 6,284,539 B1 | 9/2001 | Bowen et al. | |
| 6,417,177 B1 | 7/2002 | Nelson | |
| 6,511,800 B1 | 1/2003 | Singh | |
| 6,664,397 B1 | 12/2003 | Fletcher et al. | |
| 7,084,157 B2 | 8/2006 | Raut | |
| 7,183,112 B2 | 2/2007 | Charous | |
| 2002/0198231 A1 | 12/2002 | Nelson | |
| 2003/0119026 A1 | 6/2003 | Le et al. | |
| 2004/0167162 A1 | 8/2004 | Charous | |
| 2004/0220221 A1* | 11/2004 | Baker et al. ................... | 514/313 |
| 2004/0248893 A1 | 12/2004 | Hintermann et al. | |
| 2005/0186591 A1 | 8/2005 | Bumcrot et al. | |
| 2006/0035929 A1 | 2/2006 | Giulian et al. | |
| 2006/0119026 A1 | 6/2006 | Ryaboy et al. | |
| 2006/0121488 A1 | 6/2006 | Rothstein | |
| 2006/0129439 A1 | 6/2006 | Giulian et al. | |

FOREIGN PATENT DOCUMENTS

| | | | |
|---|---|---|---|
| WO | WO 01/91535 | * | 12/2001 |
| WO | WO 2004/066940 | | 8/2004 |
| WO | WO 2006/108666 | | 10/2006 |
| WO | WO 2007/082206 | | 7/2007 |

OTHER PUBLICATIONS

Ardayfio et al., "Impaired Learning and Memory in Pitx3 Deficient Aphakia Mice: A Genetic Model for Striatum-Dependent Cognitive Symptoms in Parkinson's Disease," *Neurobiol. Dis.* 31(3): 406-412, 2008.
Bonifati, "Genetics of Parkinson's Disease," *Minerva Med.* 96(3): 175-186, 2005.
Bonifati, "Genetics of Parkinsonism," *Parkinsonism Relat. Disord.* 13(Suppl.): S233-S241, 2007.
Bonta et al., "Nuclear Receptors Nurr77, Nurr1, and NOR-1 Expressed in Atherosclerotic Lesion Macrophages Reduce Lipid Loading and Inflammatory Responses," *Arterioscler. Thromb. Vasc. Biol.* 26(10): 2288-2294, 2006.
Castillo et al., "Dopamine Biosynthesis is Selectively Abolished in Substantia Nigra/Ventral Tegmental Area but Not in Hypothalamic Neurons in Mice with Targeted Disruption of the Nurr1 Gene," *Mol. Cell Neurosci.* 11(1-2): 36-46, 1998.
Choi et al., "Immortalization of Embryonic Mesencephalic Dopaminergic Neurons by Somatic Cell Fusion," *Brain Res.* 552(1): 67-76, 1991.
Chu et al., "Age-Related Decreases in Nurr1 Immunoreactivity in the Human Substantia Nigra," *J. Comp. Neurol.* 450(3): 203-214, 2002.
Chu et al., "Nurr1 in Parkinson's Disease and Related Disorders," *J. Comp. Neurol.* 494(3): 495-514, 2006, Author Manuscript, 1-28.
Chung et al., "Analysis of Different Promoter Systems for Efficient Transgene Expression in Mouse Embryonic Stem Cell Lines," *Stem Cells* 20(2): 139-145, 2002, Author Manuscript, 1-12.
Chung et al., "Genetic Engineering of Mouse Embryonic Stem Cells by Nurr1 Enhances Differentiation and Maturation into Dopaminergic Neurons," *Eur. J. Neurosci.* 16(10): 1829-1838, 2002, Author Manuscript, 1-23.
Cookson et al., "How Genetics Research in Parkinson's Disease is Enhancing Understanding of the Common Idiopathic Forms of the Disease," *Curr. Opin. Neurol.* 18(6): 706-711, 2005.
D'Amato et al., "Neuromelanin: A Role in MPTP-Induced Neurotoxicity," *Life Sci.* 40: 705-712, 1987.
D'Amato et al., "Evidence for Neuromelanin Involvement in MPTP-Induced Neurotoxicity," *Nature*, 327(6120): 324-326, 1987.
D'Amato et al., "Characterization of the Binding of N-Methyl-4-Phenylpyridine, the Toxic Metabolite of the Parkinsonian Neurotoxin N-Methyl-4-Phenyl-1,2,3,6-tetrahydropyridine, to Neuromelanin," *J. Neurochem.* 48(2): 653-658, 1987.
Deacon et al., "Blastula-Stage Stem Cells Can Differentiate into Dopaminergic and Serotonergic Neurons After Transplantation," *Exp. Neurol.* 149(1): 28-41, 1998.

(Continued)

*Primary Examiner* — Kevin K. Hill
(74) *Attorney, Agent, or Firm* — Clark & Elbing LLP

(57) ABSTRACT

The invention features methods and kits for treating or inhibiting the development of Parkinson's Disease by administering 7-chloro-4-aminoquinoline compounds, e.g., amodiaquine or glafenine. Stem cells are also useful in the methods of the invention and may be administered separately from or together with 7-chloro-4-aminoquinoline compounds. The invention further features methods of identifying additional chemical compounds that are useful in the treatment or inhibition of the development of Parkinson's Disease.

1 Claim, 10 Drawing Sheets

OTHER PUBLICATIONS

Farooqui et al., "Inhibitors of Brain Phospholipase A2 Activity: Their Neuropharmacological Effects and Therapeutic Importance for the Treatment of Neurologic Disorders," *Pharmacol. Rev.* 58(3): 591-620, 2006.

Giulian et al., "The Role of Mononuclear Phagocytes in Wound Healing After Traumatic Injury to Adult Mammalian Brain," *J. Neurosci.* 9(12): 4416-4429, 1989.

Hartikka et al., "Cyclic AMP, but Not Basic FGF, Increases the In Vitro Survival of Mesencephalic Dopaminergic Neurons and Protects Them from MPP(+)-Induced Degeneration," *J. Neurosci. Res.* 32(2): 190-201, 1992.

Holmin and Mathiesen, "Dexamethasone and Colchicine Reduce Inflammation and Delayed Oedema Following Experimental Brain Contusion," *Acta. Neurochir.* 138(4): 418-424, 1996.

Hulley et al., "Cyclic AMP Promotes the Survival of Dopaminergic Neurons In Vitro and Protects Them from the Toxic Effects of MPP+," *J. Neural. Transm.* 46(Suppl): 217-228, 1995.

Hwang et al., "3,4-Dihydroxyphenylalanine Reverses the Motor Deficits in Pitx3-Deficient Aphakia Mice: Behavioral Characterization of a Novel Genetic Model of Parkinson's Disease," *J. Neurosci.* 25(8): 2132-2137, 2005.

Ichinose et al., "Molecular Cloning of the Human Nurr1 Gene: Characterization of the Human Gene and cDNAs," *Gene* 230(2): 233-239, 1999.

Jaeger et al., "Aromatic L-Amino Acid Decarboxylase in the Rat Brain: Coexistence with Vasopressin in Small Neurons of the Suprachiasmatic Nucleus," *Brain Res.* 276(2): 362-366, 1983.

Kim et al., "MPP(+) Downregulates Mitochondrially Encoded Gene Transcripts and Their Activities in Dopaminergic Neuronal Cells: Protective Role of Bcl-2," *Biochem. Biophys. Res. Commun.*, 286(3): 659-665, 2001.

Kim et al., "Dopamine Neurons Derived from Embryonic Stem Cells Function in an Animal Model of Parkinson's Disease," *Nature* 418(6893): 50-56, 2002.

Kim et al., "Orphan Nuclear Receptor Nurr1 Directly Transactivates the Promoter Activity of the Tyrosine Hydroxylase Gene in a Cell-Specific Manner," *J. Neurochem.*, 85(3): 622-634, 2003.

Le et al., "Mutations in NR4A2 Associated with Familial Parkinson Disease," *Nat. Genet.* 33(1): 85-89, 2003.

Lee et al., "Efficient Generation of Midbrain and Hindbrain Neurons from Mouse Embryonic Stem Cells," *Nat. Biotechnol.* 18(6): 675-679, 2000.

Lin et al., "A Non-Peptidyl Neurotrophic Small Molecule for Midbrain Dopaminergic Neurons," *J. Neurochem.* 89(6): 1387-1395, 2004.

Martinez-González et al., "The NR4A Subfamily of Nuclear Receptors: New Early Genes Regulated by Growth Factors in Vascular Cells," *Cardiovasc. Res.* 65(3): 609-618, 2005.

Maxwell and Muscat, "The NR4A Subgroup: Immediate Early Response Genes with Pleiotropic Physiological Roles," *Nucl. Recept. Signal.* 4: e002, 2006.

Nagatsu et al., "Tyrosine Hydroxylase. The Initial Step in Norepinephrine Biosynthesis," *J. Biol. Chem.* 239(9): 2910-2917, 1964.

Ojeda et al., "Rapid Increase of Nurr1 Expression in the Substantia Nigra after 6-Hydroxydopamine Lesion in the Striatum of the Rat," *J. Neurosci. Res.* 73(5): 686-697, 2003.

Ordentlich et al., "Identification of the Antineoplastic Agent 6-Mercaptopurine as an Activator of the Orphan Nuclear Hormone Receptor Nurr1," *J. Biol. Chem.* 278(27): 24791-24799, 2003.

Pei et al., "Induction of NR4A Orphan Nuclear Receptor Expression in Macrophages in Response to Inflammatory Stimuli," *J. Biol. Chem.* 280(32): 29256-29262, 2005.

Pei et al., "Regulation of Macrophage Inflammatory Gene Expression by the Orphan Nuclear Receptor Nur77," *Mol. Endocrinol.* 20(4): 786-794, 2006.

Pires et al., "Activation of Nuclear Receptor Nurr77 by 6-Mercaptopurine Protects Against Neointima Formation," *Circulation* 115(4): 493-500, 2007.

Popert et al., "Chloroquine Diphosphate in Rheumatoid Arthritis. A Controlled Trial," *Ann. Rheum. Dis.* 20(1): 18-35, 1961.

Rynes, "Antimalarial Drugs in the Treatment of Rheumatological Diseases," *British J. Rheumatol.* 36(7): 799-805, 1997.

Sakaruda et al., "Nurr1, an Orphan Nuclear Receptor, is a Transcriptional Activator of Endogenous Tyrosine Hydroxylase in Neural Progenitor Cells Derived from the Adult Brain," *Development* 126(18): 4017-4026, 1999.

Salako, "Toxicity and Side-Effects of Antimalarials in Africa: a Critical Review," *Bull. World Health Organ.*, 62(Suppl.): 63-68, 1984.

Saucedo-Cardenas et al., "Nurr1 is Essential for the Induction of the Dopaminergic Phenotype and the Survival of Ventral Mesencephalic Late Dopaminergic Precursor Neurons," *Proc. Natl. Acad. Sci. U.S. A.*, 95(7): 4013-4018, 1998.

Temple et al., "Amodiaquine Hydrochloride—Draft Revised Poisons Information Monograph for Peer Review," http://www.who.int/ipcs/poisons/pim_amodiaquine.pdf, 2007.

Wang et al., "Structure and Function of Nurr1 Identifies a Class of Ligand-Independent Nuclear Receptors," *Nature* 423(6939): 555-560, 2003.

Witta et al., "Nigrostriatal Innervation is Preserved in Nurr1-Null Mice, Although Dopaminergic Neuron Precursors are Arrested from Terminal Differentiation," *Mol. Brain Res.* 84(1-2): 67-78, 2000.

Zetterstrom et al., "Dopamine Neuron Agenesis in Nurr1-Deficient Mice," *Science* 276(5310): 248-250, 1997.

International Search Report for WO 2007/098047, mailed Sep. 15, 2008.

International Preliminary Report on Patentability for WO 2007/098047, issued Oct. 8, 2008.

* cited by examiner

Number of TH+ cell by IHC analysis

```
SEQUENCE LISTING

<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ggcattgtga tggactccgg                                                       20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tgccacagga ttccataccc                                                       20

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ttggctgacc gcacatttg                                                        19

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 4
acgagaggca tagttcctga gc                                              22

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gggtttgagg cacacattga taag                                            24

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gcggaagaag ttgaccttgt cc                                              22

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
catggacctc accaacactg                                                 20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gagacaggtg tcttcctctg                                                 20
```

METHODS AND COMPOSITIONS FOR THE TREATMENT OF PARKINSON'S DISEASE

CROSS-REFERENCE TO RELATED APPLICATIONS

This application is the U.S. national stage of International Application No. PCT/US2007/004172, filed Feb. 15, 2007, which claims benefit of U.S. Provisional Application No. 60/743,304, filed Feb. 16, 2006, each of which is hereby incorporated by reference.

SEQUENCE LISTING

The present application contains a Sequence Listing which has been submitted in ASCII format via EFS-Web and is hereby incorporated by reference in its entirety. Said ASCII copy, created on May 31, 2011, is named 48431502_ST25.txt and is 2,177 bytes in size.

BACKGROUND OF THE INVENTION

Parkinson's Disease (PD) is a chronic, progressive motor system disorder. Approximately 50,000 Americans are diagnosed with PD each year. The primary symptoms of this neurodegenerative disease are trembling, rigidity, slowness of movement, and impaired balance. In addition, many PD patients experience a variety of other symptoms, including emotional changes, memory loss, speech problems, or difficulty sleeping.

PD is caused by specific and progressive neuronal loss of mid-brain dopamine (DA) neurons. Ordinarily, these neurons produce dopamine, a chemical messenger responsible for transmitting signals between the substantia nigra and the corpus striatum, resulting in smooth, purposeful muscle activity. However, loss of dopamine causes the nerve cells of the striatum to fire in an uncontrolled manner, leaving patients with impaired ability to direct and control their movements.

Current therapy for PD relies heavily on replenishing dopamine by giving patients oral doses of the dopamine precursor L-DOPA (L-dihydroxyphenyl-alanine). This therapy requires increasing doses as treatment continues, and it eventually elicits serious side effects. There is a need for additional therapeutics for PD.

SUMMARY OF THE INVENTION

Applicants have developed novel treatments for Parkinson's Disease, methods for causing the differentiation of stem cells into dopaminergic neurons, and screening methods useful for identification of chemical compounds for the treatment of Parkinson's Disease.

Accordingly, in one instance, the invention features a method for treating or inhibiting the development of Parkinson's Disease that includes the steps of: (a) determining whether a patient has or is at risk of developing Parkinson's Disease, and (b) if the patient has or is at risk of developing Parkinson's Disease, administering to the patient a 7-chloro-4-aminoquinoline compound, e.g., amodiaquine or glafenine, in an amount sufficient to treat or inhibit the development of Parkinson's Disease, or alternatively in an amount sufficient to activate Nurr1 in cells of the patient.

In another instance, the invention features a kit that includes a 7-chloro-4-aminoquinoline compound together with instructions for administering the compound to a patient diagnosed with or at risk of developing Parkinson's Disease.

The invention further features a method for causing the differentiation of an ex vivo stem cell, e.g., a human embryonic stem cell, into a dopaminergic neuron by contacting the stem cell with a 7-chloro-4-aminoquinoline compound that is present in an amount sufficient to induce differentiation of the stem cell.

The invention additionally features a method for treating or inhibiting the development of Parkinson's Disease that includes the steps of: (a) injecting a composition containing stem cells into the brain of a patient; and (b) following step (a), administering to the patient a 7-chloro-4-aminoquinoline compound in an amount sufficient to induce differentiation of the stem cells.

The invention further features a method for treating or inhibiting the development of Parkinson's Disease by injecting into the brain of a patient a composition containing stem cells and a 7-chloro-4-aminoquinoline compound.

In another instance, the invention features a pharmaceutical composition containing stem cells and a 7-chloro-4-aminoquinoline compound.

The invention additionally features a method for identifying a chemical compound for therapeutic use in Parkinson's Disease that includes the steps of: (a) cotransfecting a mammalian cell, e.g., SK-N-BE(2)C cell, with a first plasmid containing a domain of a Nurr1 gene and a second plasmid containing a promoter operably linked to a reporter gene; (b) contacting the cell with a candidate chemical compound; (c) measuring the resulting level of expression of the reporter gene; and (d) comparing the expression level of the reporter gene to a control value, such that, if the expression level is at least 20% greater than the control value, the candidate chemical compound is identified as a chemical compound for therapeutic use in Parkinson's Disease. In some cases, the mixture produced in step (b) is incubated for eighteen hours prior to step (c). The molar ratio between the first plasmid and the second plasmid can be any ratio, e.g., between 0.1 and 10. The second plasmid can include all or part of a tyrosine hydroxylase promoter, e.g., 100 bases or 2,600 bases of a tyrosine hydroxylase promoter. Any reporter gene, e.g., firefly luciferase, may be used. In some cases, the first plasmid contains a GAL4 DNA-binding domain operably linked to the Nurr1 domain gene, and the second plasmid contains a GAL4 binding site operably linked to the reporter gene.

The invention further features a method for identifying a chemical compound for therapeutic use in Parkinson's Disease that includes the steps of: (a) providing a mammalian cell capable of producing dopamine and a chemical compound identified using a method of the invention; (b) contacting the cell with the chemical compound so identified; (c) measuring the resulting level of expression of tyrosine hydroxylase or dopamine; and (d) comparing the expression level to a control value, such that, if the expression level is at least 20% greater than the control value, the chemical compound is identified as a chemical compound for therapeutic use in Parkinson's Disease. The measuring of step (c) can include, e.g., quantification of tyrosine hydroxylase using real time PCR or immunostaining, or quantification of dopamine using HPLC analysis. The identification of step (a) can include the use of any method of compound identification; for example, one may use a method that includes the steps of: (i) cotransfecting a mammalian cell, e.g., a SK-N-BE(2)C cell, with a first plasmid containing a domain of a Nurr1 gene and a second plasmid containing a promoter operably linked to a reporter gene; (ii) contacting the cell with a candidate chemical compound; (iii) measuring the resulting level of expression of the reporter gene; and (iv) comparing the expression level of the reporter gene to a control value, such that, if the expression level is at least 20% greater than the control value, the candidate chemical compound is identified as a chemical compound for therapeutic use in Parkinson's Disease.

In any of the methods, compositions, and kits of the invention, the 7-chloro-4-aminoquinoline compound utilized can be, e.g., amodiaquine or glafenine. Stem cells suitable for use in any of the methods, compositions, and kits of the invention include, e.g., human embryonic stem cells.

As discussed above, some of the methods of the invention employ a 7-chloro-4-aminoquinoline compound. These compounds have the formula:

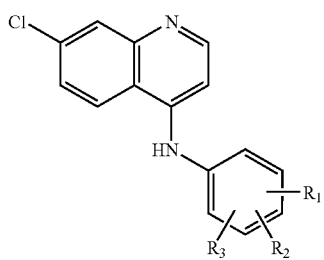

(I)

where each of $R_1$, $R_2$, and $R_3$ is, independently, selected from H, OH, OC(O)—$R_4$, C(O)—O—$R_5$, halogen, $C_{1-7}$ alkyl, $C_{2-7}$ alkenyl, $C_{2-7}$ alkynyl, and $C_{1-7}$ heteroalkyl; and each of $R_4$ and $R_5$ is, independently, selected from $C_{1-7}$ alkyl, $C_{2-7}$ alkenyl, $C_{2-7}$ alkynyl, and $C_{1-7}$ heteroalkyl. Such compounds can be prepared, for example, as described in U.S. Pat. Nos. 2,474,821 and 3,232,944, each of which is incorporated herein by reference. Exemplary commercially available 7-chloro-4-aminoquinoline compounds are amodiaquine and glafenine:

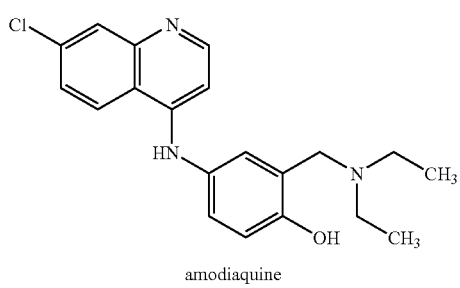

amodiaquine (II)

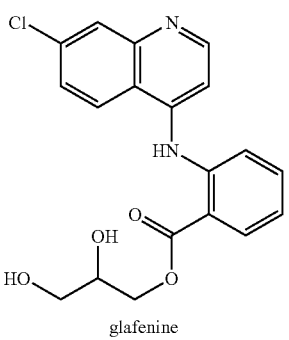

glafenine (III)

Other 7-chloro-4-aminoquinoline compounds which can be used in the methods and kits of the invention include 4-(3'-N-piperidylmethyl-4'-hydroxyanilino)-7-chloroquinone; 4-(3'-diethylaminomethyl-4'-hydroxyanilino)-7-chloroquinone; 4-(3'-ethylaminoethyl-4'-hydroxyanilino)-7-chloroquinone; 4-(3'-di-n-butylaminomethyl-4'-hydroxyanilino)-7-chloroquinone; 4-(3'-N-piperidylmethyl-4',6'-dihydroxyanilino)-7-chloroquinone; 4-(3'-diethylaminomethyl-4'-hydroxyanilino)-7-chloroquinone; 2-((7-chloro-4-quinolinyl)amino)-benzoic acid; benzoic acid, 2-((7-chloro-4-quinolinyl)amino)-, methylester; and benzoic acid, 2-((7-chloro-4-quinolinyl)amino)-, ethylester.

In the generic descriptions of compounds of this invention, the number of atoms of a particular type in a substituent group is generally given as a range, e.g., an alkyl group containing from 1 to 7 carbon atoms or $C_{1-7}$ alkyl. Reference to such a range is intended to include groups having each of the integer number of atoms within the specified range. For example, an alkyl group from 1 to 7 carbon atoms includes each of $C_1$, $C_2$, $C_3$, $C_4$, $C_5$, $C_6$, and $C_7$. A $C_{1-7}$ heteroalkyl, for example, includes from 1 to 6 carbon atoms in addition to one or more heteroatoms. Other numbers of atoms and other types of atoms may be indicated in a similar manner.

As used herein, the terms "alkyl" and the prefix "alk-" are inclusive of both straight chain and branched chain groups and of cyclic groups, i.e., cycloalkyl. Cyclic groups can be monocyclic or polycyclic and preferably have from 3 to 6 ring carbon atoms, inclusive. Exemplary cyclic groups include cyclopropyl, cyclobutyl, cyclopentyl, and cyclohexyl groups. The $C_{1-7}$ alkyl group may be substituted or unsubstituted. Exemplary substituents include alkoxy, aryloxy, sulfhydryl, alkylthio, arylthio, halide, hydroxyl, fluoroalkyl, perfluoralkyl, amino, aminoalkyl, disubstituted amino, quaternary amino, hydroxyalkyl, carboxyalkyl, and carboxyl groups. $C_{1-7}$ alkyls include, without limitation, methyl; ethyl; n-propyl; isopropyl; cyclopropyl; cyclopropylmethyl; cyclopropylethyl; n-butyl; iso-butyl; sec-butyl; tert-butyl; cyclobutyl; cyclobutylmethyl; cyclobutylethyl; n-pentyl; cyclopentyl; cyclopentylmethyl; cyclopentylethyl; 1-methylbutyl; 2-methylbutyl; 3-methylbutyl; 2,2-dimethylpropyl; 1-ethylpropyl; 1,1-dimethylpropyl; 1,2-dimethylpropyl; 1-methylpentyl; 2-methylpentyl; 3-methylpentyl; 4-methylpentyl; 1,1-dimethylbutyl; 1,2-dimethylbutyl; 1,3-dimethylbutyl; 2,2-dimethylbutyl; 2,3-dimethylbutyl; 3,3-dimethylbutyl; 1-ethylbutyl; 2-ethylbutyl; 1,1,2-trimethylpropyl; 1,2,2-trimethylpropyl; 1-ethyl-1-methylpropyl; 1-ethyl-2-methylpropyl; and cyclohexyl.

By "$C_{2-7}$ alkenyl" is meant a branched or unbranched hydrocarbon group containing one or more double bonds and having from 2 to 7 carbon atoms. A $C_{2-7}$ alkenyl may optionally include monocyclic or polycyclic rings, in which each ring desirably has from three to six members. The $C_{2-7}$ alkenyl group may be substituted or unsubstituted. Exemplary substituents include alkoxy, aryloxy, sulfhydryl, alkylthio, arylthio, halide, hydroxyl, fluoroalkyl, perfluoralkyl, amino, aminoalkyl, disubstituted amino, quaternary amino, hydroxyalkyl, carboxyalkyl, and carboxyl groups. $C_{2-7}$ alkenyls include, without limitation, vinyl; allyl; 2-cyclopropyl-1-ethenyl; 1-propenyl; 1-butenyl; 2-butenyl; 3-butenyl; 2-methyl-1-propenyl; 2-methyl-2-propenyl; 1-pentenyl; 2-pentenyl; 3-pentenyl; 4-pentenyl; 3-methyl-1-butenyl; 3-methyl-2-butenyl; 3-methyl-3-butenyl; 2-methyl-1-butenyl; 2-methyl-2-butenyl; 2-methyl-3-butenyl; 2-ethyl-2-propenyl; 1-methyl-1-butenyl; 1-methyl-2-butenyl; 1-methyl-3-butenyl; 2-methyl-2-pentenyl; 3-methyl-2-pentenyl; 4-methyl-2-pentenyl; 2-methyl-3-pentenyl; 3-methyl-3-pentenyl; 4-methyl-3-pentenyl; 2-methyl-4-pentenyl; 3-methyl-4-pentenyl; 1,2-dimethyl-1-propenyl; 1,2-dimethyl-1-butenyl; 1,3-dimethyl-1-butenyl; 1,2-dimethyl-2-butenyl; 1,1-dimethyl-2-butenyl; 2,3-dimethyl-2-butenyl; 2,3-dimethyl-3-butenyl; 1,3-dimethyl-3-butenyl; 1,1-dimethyl-3-butenyl and 2,2-dimethyl-3-butenyl.

By "C$_{2-7}$ alkynyl" is meant a branched or unbranched hydrocarbon group containing one or more triple bonds and having from 2 to 7 carbon atoms. A C$_{2-7}$ alkynyl may optionally include monocyclic, bicyclic, or tricyclic rings, in which each ring desirably has five or six members. The C$_{2-7}$ alkynyl group may be substituted or unsubstituted. Exemplary substituents include alkoxy, aryloxy, sulfhydryl, alkylthio, arylthio, halide, hydroxy, fluoroalkyl, perfluoralkyl, amino, aminoalkyl, disubstituted amino, quaternary amino, hydroxyalkyl, carboxyalkyl, and carboxyl groups. C$_{2-7}$ alkynyls include, without limitation, ethynyl, 1-propynyl, 2-propynyl, 1-butynyl, 2-butynyl, 3-butynyl, 1-pentynyl, 2-pentynyl, 3-pentynyl, 4-pentynyl, 5-hexene-1-ynyl, 2-hexynyl, 3-hexynyl, 4-hexynyl, 5-hexynyl; 1-methyl-2-propynyl; 1-methyl-2-butynyl; 1-methyl-3-butynyl; 2-methyl-3-butynyl; 1,2-dimethyl-3-butynyl; 2,2-dimethyl-3-butynyl; 1-methyl-2-pentynyl; 2-methyl-3-pentynyl; 1-methyl-4-pentynyl; 2-methyl-4-pentynyl; and 3-methyl-4-pentynyl.

By "C$_{1-7}$ heteroalkyl" is meant a branched or unbranched alkyl, alkenyl, or alkynyl group having from 1 to 7 carbon atoms in addition to 1, 2, 3 or 4 heteroatoms independently selected from the group consisting of N, O, S, and P. Heteroalkyls include, without limitation, tertiary amines, secondary amines, ethers, thioethers, amides, thioamides, carbamates, thiocarbamates, hydrazones, imines, phosphodiesters, phosphoramidates, sulfonamides, and disulfides. A heteroalkyl may optionally include monocyclic, bicyclic, or tricyclic rings, in which each ring desirably has three to six members. The heteroalkyl group may be substituted or unsubstituted. Exemplary substituents include alkoxy, aryloxy, sulfhydryl, alkylthio, arylthio, halide, hydroxyl, fluoroalkyl, perfluoralkyl, amino, aminoalkyl, disubstituted amino, quaternary amino, hydroxyalkyl, hydroxyalkyl, carboxyalkyl, and carboxyl groups.

By "administering" is meant a method of giving a dosage of a drug to a patient. The compositions utilized in the methods of the invention can be administered by a route selected from, without limitation, inhalation, ocular, parenteral, dermal, transdermal, buccal, rectal, sublingual, perilingual, nasal, topical administration and oral administration. Parenteral administration includes intravenous, intraperitoneal, subcutaneous, and intramuscular administration. The preferred method of administration can vary depending on various factors, e.g., the components of the composition being administered and the severity of the condition being treated.

By "an amount sufficient to treat" is meant the amount of a compound required to improve, inhibit, or ameliorate a condition of a patient, or a symptom of a disease, in a clinically relevant manner. Any improvement in the patient is considered sufficient to achieve treatment. A sufficient amount of an active compound used to practice the present invention for the treatment of Parkinson's Disease varies depending upon the manner of administration, the age, body weight, and general health of the patient. Ultimately, the prescribers or researchers will decide the appropriate amount and dosage regimen.

By "an amount sufficient to activate Nurr1 in a cell" is meant the amount of a compound of the invention required to increase, in a detectable and reproducible fashion, the transcription of a gene operably linked to a tyrosine hydroxylase promoter in the cell. Desirably, the increase in transcription is at least 10%, 20%, 30%, 40%, 50%, 60%, 70%, 80%, 90% or 100% relative to a reference or to a control level. The gene may be either tyrosine hydroxylase or a reporter gene, e.g., firefly luciferase. Because the tyrosine hydroxylase promoter is a direct target of Nurr1, tyrosine hydroxylase activation indicates an increase in Nurr1 levels.

By "an amount sufficient to induce differentiation" of a stem cell is meant the amount of a compound of the invention required to cause an undifferentiated stem cell to differentiate into a desired cell type, e.g., a neuron.

By "candidate chemical compound" is meant any chemical compound that is assayed for its ability to alter gene or protein expression levels, or the biological activity of a gene or protein by employing one of the assay methods described herein. Candidate compounds include, for example, peptides, polypeptides, synthesized organic molecules, naturally occurring organic molecules, nucleic acid molecules, and components thereof.

By "differentiation" is meant the process whereby an unspecialized stem cell acquires the features of a specialized cell, e.g., a nerve cell. Differentiation can also refer to the restriction of the potential of a cell to self-renew and is generally associated with a change in the functional capacity of the cell. Differentiation of a stem cell can be determined by methods well known in the art, including analysis for cell markers or morphological features associated with cells of a defined differentiated state. Examples of such markers and features include measurement of glycoprotein, alkaline phosphatase, and carcinoembryonic antigen expression, where an increase in any one of these proteins is an indicator of differentiation.

By "chemical compound for therapeutic use" is meant a compound that is, within the scope of sound medical judgment, suitable for use in contact with the tissues of humans without undue toxicity, irritation, allergic response, and the like, commensurate with a reasonable benefit/risk ratio, and effective for their intended use, as well as the zwitterionic forms, where possible, of the compositions of the invention.

By "embryonic stem cell" is meant a cell, derived from an embryo at the blastocyst stage, or before substantial differentiation of the cell into the three germ layers, that can self-renew and displays morphological characteristics of undifferentiated cells, distinguishing them from differentiated cells of embryonic or adult origin. Exemplary morphological characteristics include high nuclear/cytoplasmic ratios and prominent nucleoli under a microscope. Under appropriate conditions known to the skilled artisan, embryonic stem cells can differentiate into cells or tissues of the three germ layers: endoderm, mesoderm, and ectoderm. Assays for identification of an embryonic stem cell include the ability to form a teratoma in a suitable host or to be stained for markers of an undifferentiated cell such as Oct-4.

By "hit" in the context of a screen of chemical compounds is meant a candidate compound that tests positive in a given assay. For example, in a screen in which a positive result is indicated by an increase in reporter gene activity, a candidate compound is deemed a hit if it results in a level of reporter gene activity that is above a specified threshold, e.g., 10%, 20%, 30%, 40%, 50%, 60%, 70%, 80%, 90%, 100%, 200%, or even 500% higher than a control level of activity.

By "Nurr1 biological activity" is meant any activity known to be caused in vivo or ex vivo by a Nurr1 polypeptide. For example, such activity could include activating transcription of tyrosine hydroxylase.

"Nurr1 nucleic acid" and "Nurr1 gene" are used interchangeably herein and refer to a nucleic acid that encodes all or a portion of a Nurr1 polypeptide, or is substantially identical to all or a portion of the nucleic acid sequence of Genbank Accession No. AB017586 (Ichinose et al., Gene 230: 233-239, 1999), or analog thereof.

By "Nurr1 polypeptide" is meant a polypeptide substantially identical to all or a portion of the polypeptide sequence of Genbank Accession No. BAA75666, or analog thereof, and having Nurr1 biological activity.

By "operably linked" is meant connection of a gene and one or more regulatory elements to permit gene expression when the appropriate molecules, e.g., transcriptional activator proteins, are bound to the regulatory element(s).

By "patient" is meant any human being receiving medical treatment.

By "promoter" is meant a regulatory element of a gene that facilitates the initiation of transcription of an operably linked coding region.

By "reporter gene" is meant a gene sequence that encodes a reporter molecule, e.g., an enzyme. A reporter molecule may be detectable in any detection system, including, but not limited to, fluorescent, enzyme (e.g., ELISA, as well as enzyme-based histochemical assays), radioactive, and luminescent systems. Exemplary reporter genes include firefly luciferase, green fluorescent protein (GFP), *E. coli* beta-galactosidase or glucuronidase, human placental alkaline phosphatase, and chloramphenicol acetyltransferase (CAT); other reporter genes are known in the art and may be employed as desired.

By "stem cell" is meant any cell with the potential to self-renew and, under appropriate conditions, differentiate into a dedicated progenitor cell or a specified cell or tissue. Stem cells can be pluripotent or multipotent. Stem cells include, but are not limited to embryonic stem cells, embryonic germ cells, adult stem cells, and umbilical cord blood cells.

By "substantially identical" is meant a polypeptide or nucleic acid exhibiting at least 75%, 85%, 90%, 95%, or even 99% identity to a reference amino acid or nucleic acid sequence. For polypeptides, the length of comparison sequences will generally be at least 35 amino acids, 45 amino acids, 55 amino acids, or even 70 amino acids. For nucleic acids, the length of comparison sequences will generally be at least 60 nucleotides, 90 nucleotides, or even 120 nucleotides.

Sequence identity is typically measured using publicly available computer programs. Computer program methods to determine identity between two sequences include, but are not limited to, the GCG program package (Devereux et al., Nucleic Acids Research 12: 387, 1984), BLASTP, BLASTN, and FASTA (Altschul et al., J. Mol. Biol. 215:403, 1990). The well-known Smith Waterman algorithm may also be used to determine identity. The BLAST program is publicly available from NCBI and other sources (e.g., BLAST Manual, Altschul et al., NCBI NLM NIH, Bethesda, Md. 20894). These software programs match similar sequences by assigning degrees of homology to various substitutions, deletions, and other modifications. Conservative substitutions for amino acid comparisons typically include substitutions within the following groups: glycine, alanine, valine, isoleucine, leucine; aspartic acid, glutamic acid, asparagine, glutamine; serine, threonine; lysine, arginine; and phenylalanine, tyrosine.

By "tyrosine hydroxylase promoter" is meant an upstream element of a tyrosine hydroxylase gene that is capable of regulating expression of the tyrosine hydroxylase gene by facilitating initiation of transcription. A tyrosine hydroxylase promoter may be operably linked to any gene in order to regulate the expression of that gene. Any tyrosine hydroxylase promoter may be used in the invention, e.g., as provided in Kim et al., J. Neurochem., 85:622-634, 2003.

The aspects of the invention provide a number of advantages. For example, treatment of Parkinson's Disease patients with a 7-chloro-4-aminoquinoline compound can alleviate symptoms such as impaired balance and coordination; rhythmic tremors of the arms, jaw, legs, or face; muscle rigidity; and bradykinesia, i.e., slowness of voluntary movement. Additionally, treatment of Parkinson's Disease patients with both stem cells and a 7-chloro-4-aminoquinoline compound can provide the further advantage of increasing the efficacy of the treatment, or reducing the dosage of the 7-chloro-4-aminoquinoline compound that would otherwise be required to effect treatment. The screening assays described herein are also advantageous in that they provide methods of identifying additional compounds that may be useful in the treatment of Parkinson's Disease.

Other features and advantages of the invention will be apparent from the following detailed description, and from the claims.

DETAILED DESCRIPTION OF THE INVENTION

Figure 1:
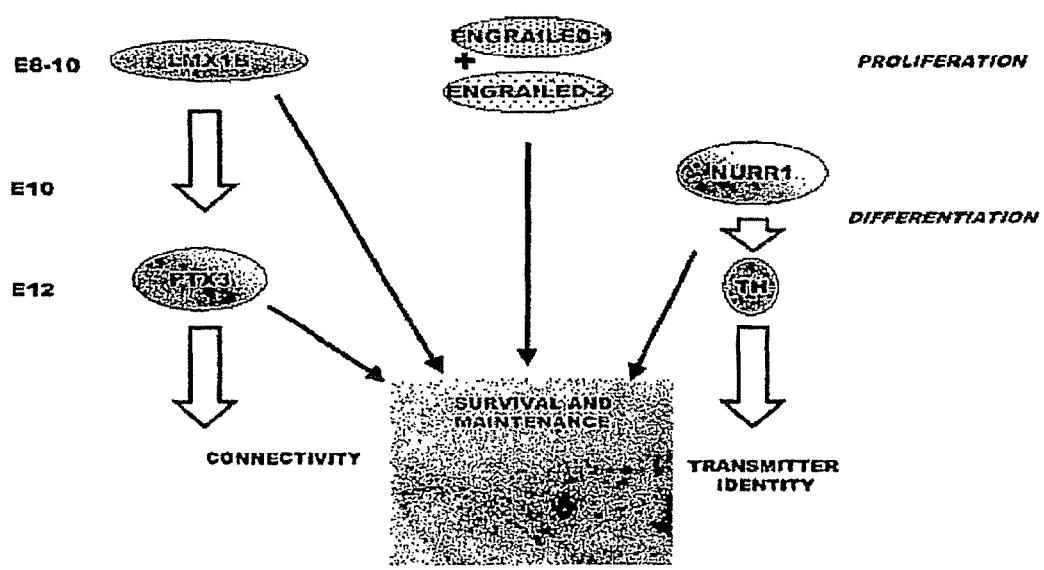
FIG. 1 is a diagram showing the role of Nurr1 in the development of dopamine neurons.

The invention features unique therapies for Parkinson's Disease. The methods of treatment feature administration of a 7-chloro-4-aminoquinoline compound in an amount sufficient to treat the disease; this generally involves administration in an amount sufficient to activate Nurr1 in a cell of the patient being treated. Stem cells may also be used in the other therapeutic aspects of the invention; for example, embryonic stem cells, bone marrow stem cells, cord blood stem cells, and peripheral blood stem cells may each be used. The invention additionally features methods for causing the differentiation of embryonic stem cells into dopaminergic neurons, such methods featuring the use of a 7-chloro-aminoquinoline compound. The invention further features screening methods useful for identification of chemical compounds for the treatment of Parkinson's Disease. The methods of identification feature screening of small molecules for activation of one or more transcription factors that play a role in promoting the survival and/or maintenance of DA neurons. For example, Nurr1, a key fate-determining transcription factor for midbrain dopamine neurons, is a useful target in the screening assays of the invention.

7-chloro-4-aminoquinoline Compounds 7-chloro-4-aminoquinoline compounds, defined above, are useful in the methods, kits, and compositions of the invention. Exemplary compounds utilized in the methods of the invention are amodiaquine, an antimalarial compound with schizonticidal activity, and glafenine, an anthranilic acid derivative with analgesic properties used for the relief of pain.
Therapy Therapy according to the invention may be performed alone or in conjunction with another therapy, and may be provided at home, the doctor's office, a clinic, a hospital's outpatient department, or a hospital. Treatment generally begins at a hospital so that the doctor can observe the therapy's effects closely and make any adjustments that are needed. The duration of the therapy depends on the age and condition of the patient, the stage of the patient's Parkinson's Disease, and how the patient responds to the treatment. Additionally, a person having a greater risk of developing Parkinson's Disease (e.g., a person who is genetically predisposed) may receive prophylactic treatment to inhibit or delay symptoms of the disease.

Methods of diagnosing patients as having or being at risk of having Parkinson's Disease are well-known in the art. For example, the presence of one or more of the following symptoms may be used as part of a PD diagnosis: trembling, e.g., an involuntary, rhythmic tremor of one arm or one leg; muscular rigidity, stiffness, or discomfort; general slowness in any of the activities of daily living, e.g., akinesia or bradykinesia; difficulty with walking, balance, or posture; alteration in handwriting; emotional changes; memory loss; speech problems; and difficulty sleeping. Review of a patient's symptoms, activity, medications, concurrent medical problems, or possible toxic exposures can be useful in making a PD diagnosis. In addition, a patient may be tested for the presence or absence of genetic mutations that can indicate an increased likelihood of having Parkinson's Disease. For example, the presence of one or more specific mutations or polymorphisms in the NURR1, alpha-synuclein, parkin, MAPT, DJ-1, PINK1, SNCA, NAT2, or LRRK2 genes may be used to diagnose a patient as having or being at risk of having Parkinson's Disease. See, e.g., U.S. Patent Application Publication Nos. 2003-0119026 and 2005-0186591; Bonifati, Minerva Med. 96:175-186, 2005; and Cookson et al., Curr. Opin. Neurol. 18:706-711, 2005, each of which is hereby incorporated by reference.

Formulation of Pharmaceutical Compositions

The pharmaceutical compositions of the invention are prepared in a manner known to those skilled in the art, for example, by means of conventional dissolving, lyophilising, mixing, granulating or confectioning processes. Methods well known in the art for making formulations are found, for example, in Remington: The Science and Practice of Pharmacy, 20th ed., ed. A. R. Gennaro, 2000, Lippincott Williams & Wilkins, Philadelphia, and Encyclopedia of Pharmaceutical Technology, eds. J. Swarbrick and J. C. Boylan, 1988-1999, Marcel Dekker, New York.

Suitable modes of administration include, but are not limited to, oral, rectal, intravenous, intramuscular, subcutaneous, inhalation, topical or transdermal, vaginal, and ophthalmic.

Administration of compositions of the invention may be by any suitable means that results in a compound concentration that is effective for treating or inhibiting (e.g., by delaying) the development of Parkinson's Disease. The compound is admixed with a suitable carrier substance, e.g., a pharmaceutically acceptable excipient that preserves the therapeutic properties of the compound with which it is administered. One exemplary pharmaceutically acceptable excipient is physiological saline. The suitable carrier substance is generally present in an amount of 1-95% by weight of the total weight of the composition. The composition may be provided in a dosage form that is suitable for oral, rectal, intravenous, intramuscular, subcutaneous, inhalation, nasal, topical or transdermal, vaginal, or ophthalmic administration. Thus, the composition may be in form of, e.g., tablets, capsules, pills, powders, granulates, suspensions, emulsions, solutions, gels including hydrogels, pastes, ointments, creams, plasters, drenches, delivery devices, suppositories, enemas, injectables, implants, sprays, or aerosols.

Pharmaceutical compositions according to the invention may be formulated to release the active compound substantially immediately upon administration or at any predetermined time period after administration, using controlled release formulations.

Administration of compounds in controlled release formulations is useful where the compound, either alone or in combination, has (i) a narrow therapeutic index (e.g., the difference between the plasma concentration leading to harmful side effects or toxic reactions and the plasma concentration leading to a therapeutic effect is small; generally, the therapeutic index, TI, is defined as the ratio of median lethal dose ($LD_{50}$) to median effective dose ($ED_{50}$)); (ii) a narrow absorption window in the gastro-intestinal tract; or (iii) a short biological half-life, so that frequent dosing during a day is required in order to sustain the plasma level at a therapeutic level.

Many strategies can be pursued to obtain controlled release in which the rate of release outweighs the rate of metabolism of the therapeutic compound. For example, controlled release can be obtained by the appropriate selection of formulation parameters and ingredients, including, e.g., appropriate controlled release compositions and coatings. Suitable formulations are known to those of skill in the art. Examples include single or multiple unit tablet or capsule compositions, oil solutions, suspensions, emulsions, microcapsules, microspheres, nanoparticles, patches, and liposomes.

Solid Formulations for Oral Use

Formulations for oral use include tablets containing the active ingredient in a mixture with non-toxic pharmaceutically acceptable excipients. These excipients may be, for example, inert diluents or fillers (e.g., sucrose and sorbitol), lubricating agents, glidants, and antiadhesives (e.g., magnesium stearate, zinc stearate, stearic acid, silicas, hydrogenated vegetable oils, or talc).

Formulations for oral use may also be provided as chewable tablets, or as hard gelatin capsules wherein the active ingredient is mixed with an inert solid diluent, or as soft gelatin capsules wherein the active ingredient is mixed with water or an oil medium.

Dosage

Appropriate dosages of compounds used in the methods of the invention depend on several factors, including the administration method, the severity of the Parkinson's Disease, and the age, weight, and health of the patient to be treated. Additionally, pharmacogenomic (the effect of genotype on the pharmacokinetic, pharmacodynamic or efficacy profile of a therapeutic) information about a particular patient may affect dosage used.

Continuous daily dosing with compounds used in the methods of the invention may not be required. A therapeutic regimen may require cycles, during which time a drug is not administered, or therapy may be provided on an as-needed basis.

As described above, the compound or composition in question may be administered orally in the form of tablets, capsules, elixirs or syrups, or rectally in the form of suppositories. Parenteral administration of a compound is suitably performed, for example, in the form of saline solutions or with the compound incorporated into liposomes. In cases where the compound in itself is not sufficiently soluble to be dissolved, a solubilizer such as ethanol can be applied.

The dosage of any of the chemical compounds used in the methods of the invention can readily be determined by one skilled in the art. Desirably, the dosage of any of the chemical compounds used in the methods of the invention will be sufficient to ameliorate a symptom of Parkinson's Disease in the patient. Alternatively, the dosage will be sufficient to activate Nurr1 in a cell of the patient. For methods of the invention involving differentiation of ex vivo stem cells, desirably the dosage will be sufficient to induce stem cell differentiation.

Below, for illustrative purposes, dosages for amodiaquine and glafenine are described. One skilled in the art will readily be able to ascertain suitable dosages for other 7-chloro-4-aminoquinoline compounds and other compounds useful in the methods of the invention.

Oral Administration

The total daily oral dosage of amodiaquine for an average adult human can be about 1-600 mg (0.02-8.5 mg/kg), preferably about 25-400 mg (0.35-5.7 mg/kg), and more preferably about 100-300 mg (1.4-4.2 mg/kg) total daily dose. Administration can be one to three times daily for one day to one year, and may even be daily administration for the life of the patient. Chronic, long-term administration will be indicated in many cases. Daily dosages up to 600 mg may be necessary.

For glafenine adapted for oral administration for systemic use, the daily dosage can be about 0.1-60 mg (0.002-0.85 mg/kg), preferably about 2.5-40 mg (0.035-0.57 mg/kg), and more preferably about 10-30 mg (0.14-0.42 mg/kg) total daily dose. Like amodiaquine, glafenine may be administered for one day to one year, and may even be for the life of the patient. Dosages up to 60 mg per day may be necessary.

Additional Routes of Administration

For intravenous, intramuscular, subcutaneous, rectal, inhalation, topical, vaginal, or ophthalmic administration of amodiaquine, a total daily dosage can be about 1-600 mg (0.02-8.5 mg/kg), preferably about 25-400 mg (0.35-5.7 mg/kg), and more preferably about 100-300 mg (1.4-4.2 mg/kg). A total daily dosage of glafenine can be about 0.1-60 mg (0.002-0.85 mg/kg), preferably about 2.5-40 mg (0.035-0.57 mg/kg), and more preferably about 10-30 mg (0.14-0.42 mg/kg). By these routes, administration of either amodiaquine or glafenine is one to four times daily.

Stem Cells

Stem cells may be utilized in conjunction with a 7-chloro-4-aminoquinoline compound in the methods, kits, and compositions of the invention. For example, the invention features methods for causing the differentiation of an ex vivo stem cell into a dopaminergic neuron by contacting the stem cell with a 7-chloro-4-aminoquinoline compound. The invention also features in vivo methods for utilizing stem cells, e.g., injection of stem cells into the brain of a patient along with administration of a 7-chloro-4-aminoquinoline compound. Thus, in light of the present invention, stem cells offer a powerful tool for treating patients suffering from disorders that include loss or deterioration of dopaminergic neurons, e.g., Parkinson's Disease.

Stem cells are unique cell populations that have the ability to divide (self-renew) for indefinite periods of time, and, under the right conditions or signals, to differentiate into the many different cell types that make up an organism. Stem cells derived from the inner cell mass of the blastocyst are known as embryonic stem (ES) cells. Stem cells derived from the primordial germ cells, and which normally develop into mature gametes (eggs and sperm) are known as embryonic germ (EG) cells. Both of these types of stem cells are known as pluripotent cells because of their unique ability to differentiate into derivatives of all three embryonic germ layers (endoderm, mesoderm, and ectoderm).

The pluripotent stem cells can further specialize into another type of multipotent stem cell often derived from adult tissues. Multipotent stem cells are also able to undergo self-renewal and differentiation, but unlike embryonic stem cells, are committed to give rise to cells that have a particular function. Examples of adult stem cells include hematopoietic stem cells (HSC), which can proliferate and differentiate to produce lymphoid and myeloid cell types; bone marrow-derived stem cells (BMSC), which can differentiate into adipocytes, chondrocytes, osteocytes, hepatocytes, cardiomyocytes and neurons; neural stem cells (NSC), which can differentiate into astrocytes, neurons, and oligodendrocytes;

and peripheral blood stem cells. Multipotent stem cells have also been derived from epithelial and adipose tissues and umbilical cord blood (UCB).

ES cells, derived from the inner cell mass of preimplantation embryos, have been recognized as the most pluripotent stem cell population and are therefore the preferred cell for the methods of the invention. These cells are capable of unlimited proliferation ex vivo, while maintaining the capacity for differentiation into a wide variety of somatic and extra-embryonic tissues. ES cells can be male (XY) or female (XX); female ES cells are preferred.

Multipotent, adult stem cells can also be used in the methods of the invention. Preferred adult stem cells include hematopoietic stem cells (HSC), which can proliferate and differentiate throughout life to produce lymphoid and myeloid cell types; bone marrow-derived stem cells (BMSC), which can differentiate into various cell types including adipocytes, chondrocytes, osteocytes, hepatocytes, cardiomyocytes and neurons; and neural stem cells (NSC), which can differentiate into astrocytes, neurons, and oligodendrocytes. Multipotent stem cells derived from epithelial and adipose tissues and umbilical cord blood cells can also be used in the methods of the invention.

Stem cells can be derived from any mammal including, but not limited to, mouse, human, and primates. Following acquisition of stem cells, these cells may be used directly in the methods of the invention; for example, umbilical cord blood cells may be acquired in sufficient quantity to use directly for therapeutic purposes. Alternatively, stem cells may first be expanded in order to increase the number of available cells; see, for example, U.S. Pat. No. 6,338,942. Preferred mouse strains for stem cell preparation include 129, C57BL/6, and a hybrid strain (Brook et al., *Proc. Natl. Acad. Sci. U.S.A.* 94:5709-5712 (1997), Baharvand et al., *In Vitro Cell Dev. Biol. Anim.* 40:76-81 (2004)). Methods for preparing mouse, human, or primate stem cells are known in the art and are described, for example, in Nagy et al., *Manipulating the mouse embryo: A laboratory manual,* 3$^{rd}$ ed., Cold Spring Harbor Laboratory Press (2002); Thomson et al., *Science* 282:1145-1147 (1998), Marshall et al., *Methods Mol. Biol.* 158:11-18 (2001); Thomson et al., *Trends Biotechnol.* 18:53-57 (2000); Jones et al., *Semin. Reprod. Med.* 18:219-223 (2000); Voss et al., *Exp. Cell Res.* 230:45-49 (1997); and Odorico et al., *Stem Cells* 19:193-204 (2001).

ES cells can be directly derived from the blastocyst or any other early stage of development, or can be a "cloned" stem cell line derived from somatic nuclear transfer and other similar procedures. General methods for culturing mouse, human, or primate ES cells from a blastocyst can be found in Appendix C of the NIH report on stem cells entitled *Stem Cells: Scientific Progress and Future Research Directions* (June 2001). For example, in the first step, the inner cell mass of a preimplantation blastocyst is removed from the trophectoderm that surrounds it. (For cultures of human ES cells, blastocysts are generated by in vitro fertilization and donated for research.) The small plastic culture dishes used to grow the cells contain growth medium supplemented with fetal calf serum, and are sometimes coated with a "feeder" layer of nondividing cells. The feeder cells are often mouse embryonic fibroblast (MEF) cells that have been chemically inactivated so they will not divide. Additional reagents, such as the cytokine leukemia inhibitory factor (LIF), can also be added to the culture medium for mouse ES cells. Second, after several days to a week, proliferating colonies of cells are removed and dispersed into new culture dishes, each of which may or may not contain an MEF feeder layer. If the cells are to be used to human therapeutic purposes, it is preferable that the MEF feeder layer is not included. Under these ex vivo conditions, the ES cells aggregate to form colonies. In the third major step required to generate ES cell lines, the individual, nondifferentiating colonies are dissociated and replated into new dishes, a step called passage. This replating process establishes a "line" of ES cells. The line of cells is termed "clonal" if a single ES cell generates it. Limiting dilution methods can be used to generate a clonal ES cell line. Reagents needed for the culture of stem cells are commercially available, for example, from Invitrogen, Stem Cell Technologies, R&D Systems, and Sigma Aldrich, and are described, for example, in U.S. Patent Publication Nos. 2004/0235159 and 2005/0037492 and Appendix C of the NIH report, *Stem Cells: Scientific Progress and Future Research Directions, supra.*

The methods for utilizing stem cells described herein can be used for the treatment of diseases treatable through transplantation of differentiated cells derived from ES cells. Stem cells of the invention or produced using the methods of the invention can be used to treat Parkinson's Disease, other neurodegenerative disorders, e.g., Alzheimer's Disease, or traumatic injury to the brain or spinal cord in any patient, preferably a human.

The invention can also be used for research purposes for the study of differentiation or development, and for the generation of transgenic animals useful for research purposes. The stem cells and methods of their use described herein can be used, for example, to create and test animal models of Parkinson's Disease or other neurological disorders. The stem cells and methods of the invention can also be used to study the effects of a particular compound on stem cell differentiation, development, and tissue generation or regeneration.

Assays and Screens to Detect Activation of Nurr1

Figure 2:
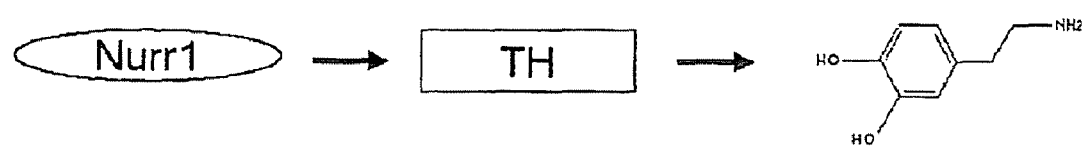
FIG. 2 is a diagram showing the relationship between Nurr1, tyrosine hydroxylase, and dopamine.

Nurr1 is a key fate-determining transcription factor for midbrain dopamine neurons (FIG. 1), and accordingly it is a useful target in the screening assays of the invention. Nurr1 directly transactivates the promoter activity of the tyrosine hydroxylase (TH) gene in a cell-specific manner (Kim et al., J. Neurochem., 85:622-634, 2003) (FIG. 2). In addition, age-related decline of dopaminergic phenotypic markers is associated with down-regulation of Nurr1 expression in the substantia nigra. Therefore, molecules that activate Nurr1 function may facilitate the neuronal survival of DA neurons and increased production of dopamine by increasing TH gene expression. Screening, e.g., high-throughput screening (HTS), of small molecule libraries may be used according to the methods of the invention.

The invention features assays for compounds that activate Nurr1 function, thereby facilitating the neuronal survival of DA neurons and increased production of dopamine by increasing TH gene expression. In one assay of the invention, an effector plasmid containing all or a portion of the Nurr1 gene is cotransfected with a reporter plasmid containing a reporter gene operably linked to a portion of native or modified tyrosine hydroxylase promoter. Reporter gene assays are performed in the presence and absence of individual candidate compounds or libraries of compounds. Various parameters including, but not limited to, plasmid ratios, portion of Nurr1 gene present in the effector plasmid, length and sequence of TH promoter, reporter gene, cell line, and reporter gene assays, may be varied individually or jointly in order to optimize screening conditions.

For example, the effector plasmid includes a gene encoding Nurr1 or a domain thereof, e.g., the LBD (ligand-binding domain), fused to a gene encoding another domain, e.g., the GAL4 DNA-binding domain (DBD). A corresponding upstream activation region of DNA, e.g., the GAL4 binding site, is operably linked to a reporter gene in a reporter plasmid. Effector and reporter plasmids are cotransfected into cells in the presence and absence of candidate compounds, and hit candidates are identified based on the results of a reporter gene assay.

Desirably, a library of candidate compounds is tested in one ex vivo assay, and the hit candidates generated from this assay are tested in a second, distinct ex vivo assay, in order to remove false positive hit candidates.

Following ex vivo screens or other studies that identify a set of hit candidate compounds, it is desirable to perform in vivo studies in order to validate the hit candidates. For example, a candidate compound may be administered to test subjects, e.g., mice; subsequently, studies may be performed on midbrain dopaminergic neurons from the test subjects in order to determine whether the hit candidate compound increased dopamine expression in comparison to control experiments.

Figure 3:
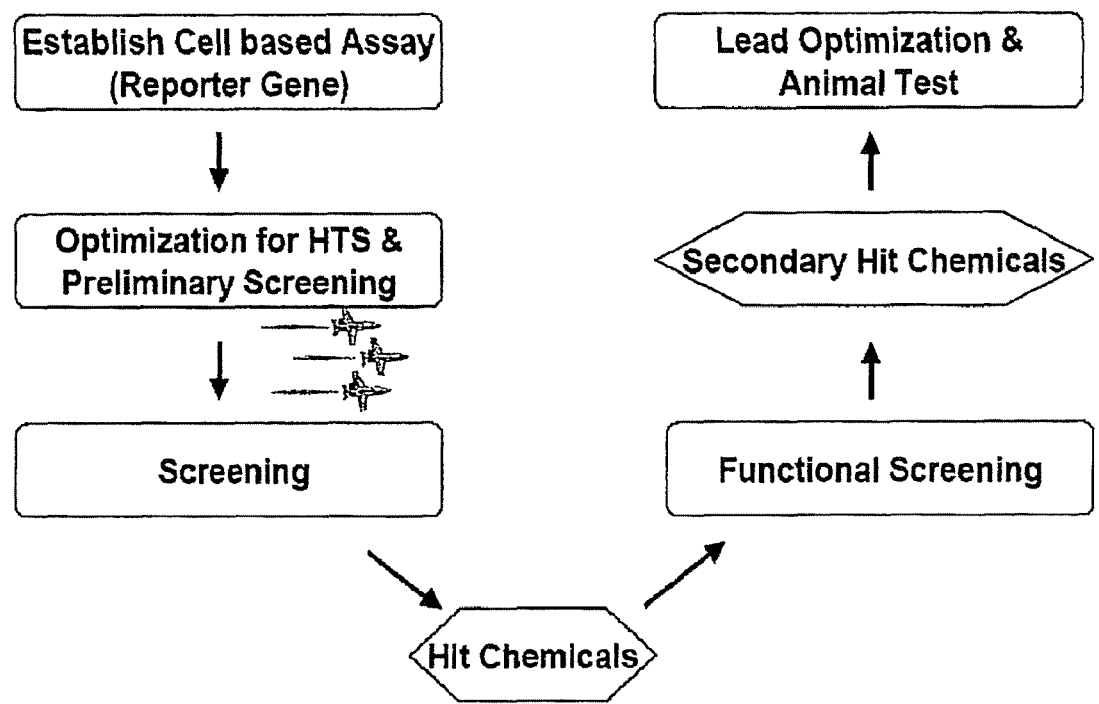
FIG. 3 is a flowchart showing a method of discovering and testing Nurr1 activators.

FIG. 3 provides an overview of the process involved in creating cell-based assays, using them to identify and refine hit candidate compounds, and testing these compounds in vivo. Detailed examples of screening and testing experiments are described below.

EXAMPLES

The following examples are provided for the purposes of illustrating the invention, and should not be construed as limiting.

Example 1

Nurr1 Cell-Based Assay System

A cell-based system exploiting Nurr1's activation of TH was created in order to develop an assay for identification of Nurr1-activating compounds. SK-N-BE(2)C (TH expressing) cells were used as a host cell line, demonstrating the clear response of Nurr1 effector to reporter plasmid in transfection. In addition, a transient transfection was selected, rather than using stable cell-line transfection, to favor the maximum responsiveness of compounds to the reporter gene in order to detect low-affinity hit chemicals in the first screening. Another parameter considered was the selection of short-sized natural TH promoters with all essential NBRE (Nurr1-binding)-like motifs rather than one specific kind of NBRE-motif, based on the assumption that the natural promoter generates closer biological screening condition than artificially copied promoter and the false positive chemicals due to the interaction of other unrelated transcription factors can be easily ruled out by the effective secondary screening method.

Figure 4:
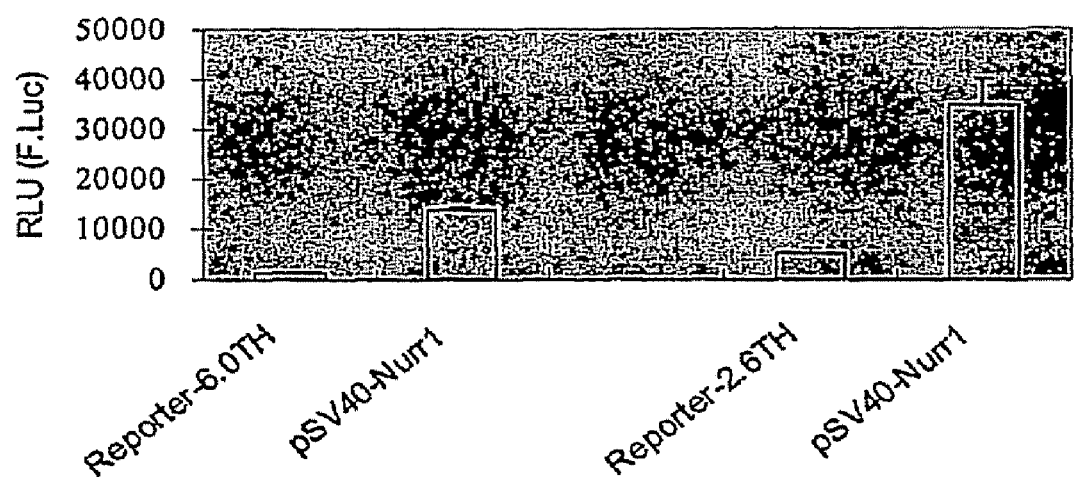
FIG. 4 is a chart showing the results of transient transfection analyses in SK-N-BE(2)C cells. Transiently expressed Nurr1 activity in SK-N-BE(2)C cells was measured by cotransfection with 2.6 kb-TH promoter and 6.0-TH promoter respectively. The molar ratio of effector plasmid to reporter plasmid used for transfection was 0.5 in each experiment. Luciferase activity was determined and normalized to the activity of beta-galactosidase as an internal control.

To explore this new Nurr1 cell based assay system, several combinations of variable parameters, including effector gene promoter, internal control gene promoter, TH promoter size, promoter of internal control gene, transient transfection condition, serum concentration, and DMSO effect were tried. For example, the effect of TH promoter size to the reporter gene was investigated (FIG. 4), showing that exogenous Nurr1 expression robustly transactivated reporter gene expression driven by 2.6 kb-TH better than 6.0 kb-TH in SK-N-BE(2)C cells.

Figure 5A:
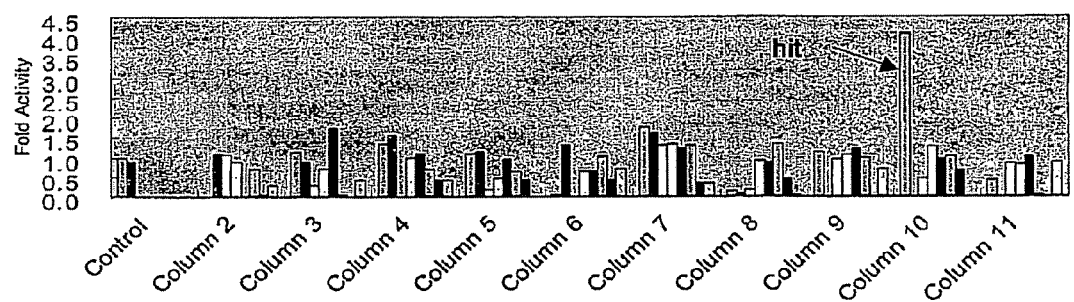
FIG. 5A is a chart showing preliminary screening data with a small chemical library. Transiently expressed Nurr1 activity in SK-N-BE(2)C cells was measured by luciferase activity with 2.6-TH promoter after incubation with each compound for eighteen hours. The cell-based assay system generated a positive hit candidate, forskolin, that showed an apparent increase in luciferase activity compared to control with DMSO. Each column has eight different chemical compounds.
Figure 5B:
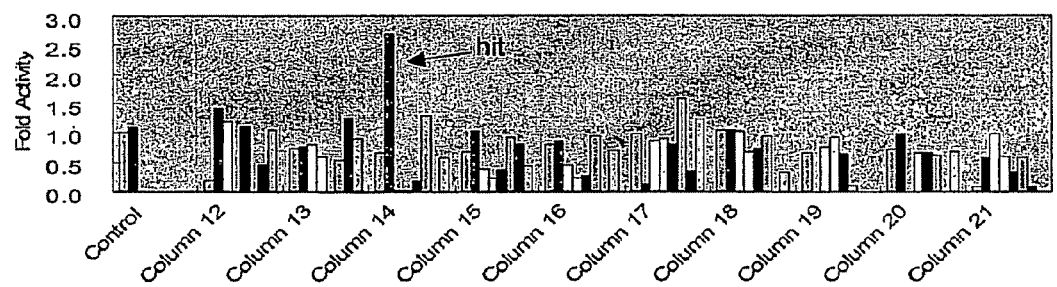
FIG. 5B is a chart showing further preliminary screening data with a small chemical library. Transiently expressed Nurr1 activity in SK-N-BE(2)C cells was measured by luciferase activity with 2.6-TH promoter after incubation with each compound for eighteen hours. The cell-based assay system generated a positive hit candidate, chloroquine diphosphate, that showed an apparent increase in luciferase activity compared to control with DMSO. Each column has eight different chemical compounds.
Figure 6:
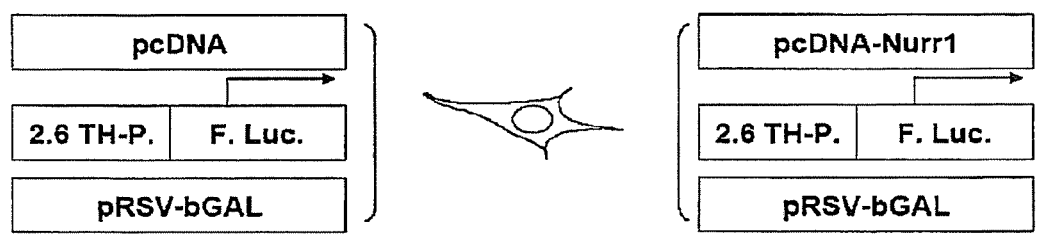
FIG. 6 includes a chart showing repeated primary screening data with primary hit candidates. Transiently expressed Nurr1 activity in SK-N-BE(2)C cells was measured by luciferase activity after incubation of each compound with the pcDNA-Nurr1 construct for eighteen hours. Two hit candidates, amodiaquine and glafenine, were identified.
Figure 6:
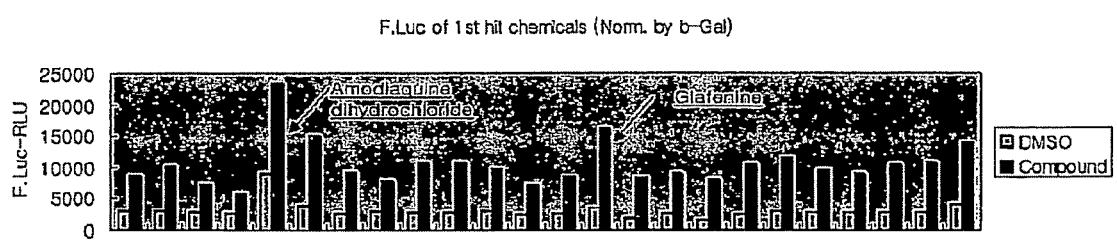

A preliminary screening of Nurr1 activators under partially optimized conditions was performed using a small chemical library. As shown in FIGS. 5A-5B and 6, some candidate compounds showed a several-fold increase in luciferase activity as compared to control.

Figure 7:
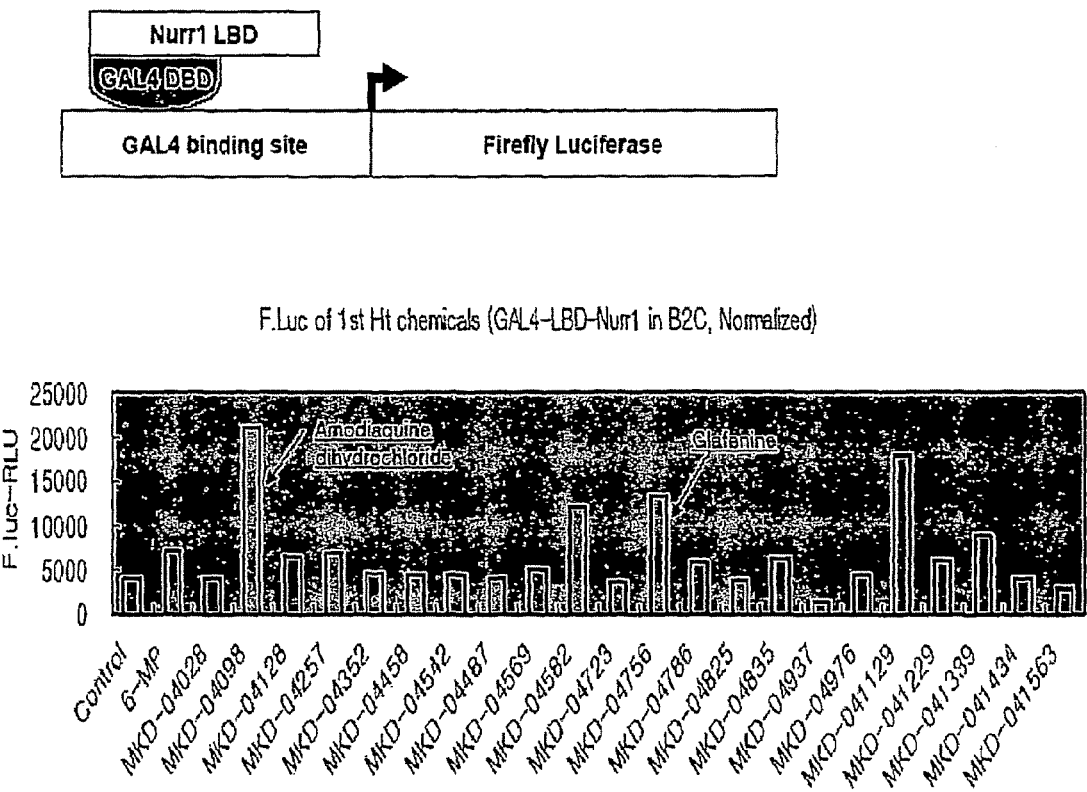
FIG. 7 includes a chart showing secondary screening data with primary hit chemicals. Transiently expressed Nurr1 activity in SK-N-BE(2)C cells was measured by luciferase activity after incubation of each compound with GAL4-DBD construct fused with Nurr1-LBD for eighteen hours. Two hit candidates, amodiaquine and glafenine, were identified. Also shown is a schematic representation of the GAL4-DBD-Nurr1-LBD fusion construct activating the firefly luciferase reporter gene.
Figure 8A:
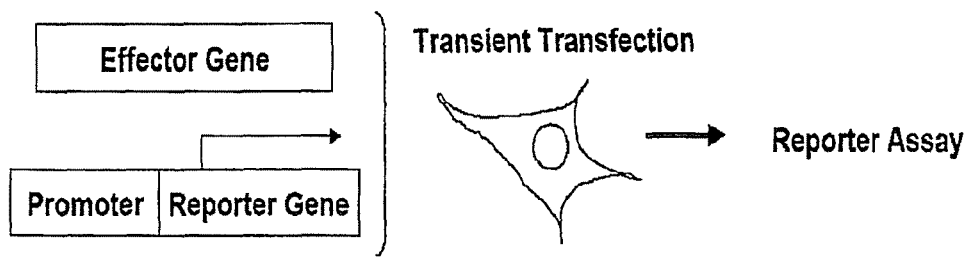
FIG. 8A is a diagram showing a transient transfection reporter assay.
Figure 8B:
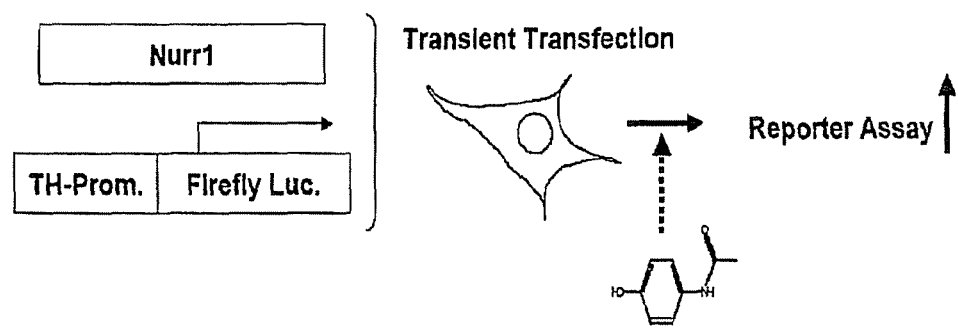
FIG. 8B is a diagram showing a transient transfection reporter assay in which Nurr1 is the effector gene, the promoter is from the TH gene, and firefly luciferase is the reporter gene.
Figure 9A:
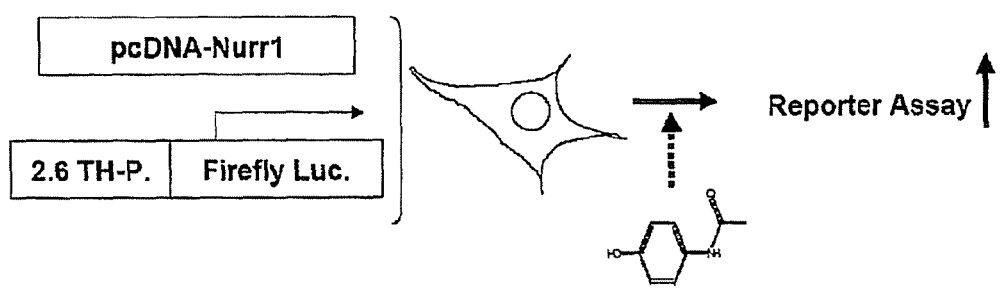
FIG. 9A is a diagram showing a transient transfection reporter assay in which pcDNA-Nurr1 is the effector gene, the promoter is from 2.6 Kb upstream of the TH gene, and firefly luciferase is the reporter gene.
Figure 9B:
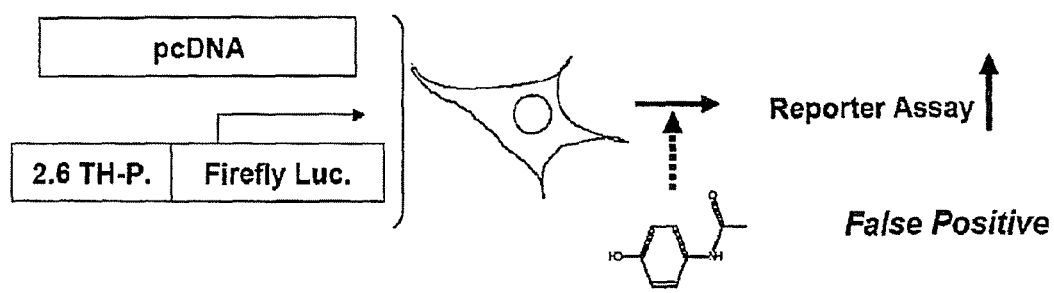
FIG. 9B is a diagram showing a transient transfection reporter assay in which no effector gene is added in the presence of the 2.6 Kb TH promoter and firefly luciferase reporter gene. Hit compounds that show increased luciferase activity in this system are determined to be false positives.

Using this approach, several primary hit candidates were identified as Nurr1 activators from initial screenings using the Nurr1 effector and the 2.6-TH promoter fused to firefly luciferase. As a secondary screening system, GAL4 DNA binding domain (DBD) constructs were used, which separately fused whole Nurr1, Nurr1-ligand binding domain (LBD), or Nurr1-DNA binding domain to the yeast GAL4 DBD. For example, the effect of primary hit candidates to the reporter gene with GAL4 DBD-Nurr1 LBD is shown in FIG. 7, which showed that this secondary system could screen out false positives from primary hit candidates. 6-MP, regulating Nurr1 through a region in the amino terminus, was used as a negative control in this experiment. Amodiaquine and glafenine were identified as hit candidate compounds in this secondary assay.

This series of experiments demonstrated the value of using both primary and secondary screens to identify lead compounds that may be useful for the treatment of Parkinson's Disease.

Example 2

Relative Activity Assay of 7-chloro-4-aminoquinoline Compounds

Human neuroblastoma SK-N-BE(2)C cells were grown in Dulbecco's modified Eagle's medium supplemented with 10% fetal calf serum (Hyclone), 100 µg/mL streptomycin, and 100 units/mL penicillin and plated at 25,000 cells/well in the above media without antibiotic into 96-well plates one day prior to transfection. Each 96-well plate was transfected with a 1:1 molar ratio of effector plasmid containing the Nurr1 gene and reporter construct containing a reporter gene (FIGS. 8A-8B and 9A-9B). Transfections were carried out by the Lipofectamine method, and plasmids for transfection were prepared using Qiagen columns (Qiagen Co., Santa Clarita, Calif., USA). The total DNA amount used per 96-well plate was 0.2 µg, with 0.02 µg of pRSV-b-gal used as an internal control. On the day of transfection, 0.2 µg of DNA was diluted in 25 µl of Opti-MEM I reduced serum media, and 0.5 µl of Lipofectamine was diluted in 25 µl of Opti-MEM media for each 96-well plate. After a five-minute incubation, the diluted DNA and the diluted Lipofectamine were combined and incubated for forty minutes at room temperature to allow the DNA-Lipofectamine complexes to form.

After removing 50 µl of the DNA-Lipofectamine complex, three compounds (amodiaquine, glafenine, and chloroquine diphosphate), each diluted at the appropriate concentration in the DMEM media with 3% charcoal-stripped fetal calf serum, were added and incubated overnight. Cells from each 96-well plate were then lysed with 50 µl of lysis buffer, which contains 25 mM Tris-phosphate (pH 7.8), 2 mM DTT, 2 mM CDTA (1,2-diaminocyclohexane-N,N,N',N'-tetraacetic acid), 10% glycerol, and 1% Triton X-100. Next, equal volumes of firefly luciferase substrate were added, and the luciferase activity was measured using a Luminometer plate reader and normalized for beta-galactosidase activity, as shown in the table below:

| DERIVATIVES (+: REL. ACTIVITY) | DISSOLVED IN DMSO | DISSOLVED IN 1xPBS |
|---|---|---|
| Amodiaquine (4E) | ++++ | ++++ |
| Glafenine (11D) | +++ | +++ |
| Chloroquine diphosphate | − | ++ |

Example 3

Establishment of an Ex Vivo Functional System to Study Hit Candidates

Ex vivo functional study systems may be set up to select the best hit candidates for further drug lead development for treatment of Parkinson's disease. One possible functional study system of Nurr1 activators consists of detecting the increase of TH gene expression by real time-PCR, dopamine amount detection by HPLC, and immunostaining of TH protein in a dopaminergic cell line.

Quantification of TH mRNA by real time-PCR. The dopamine cell line MN9D provides a useful ex vivo model for studying the function of hit candidates. MN9D was generated by a somatic cell fusion of primary neurons from mouse Embryonic Day 14 rostral mesencephalic tegmentum and the neuroblastoma cell line N18TG2 (Choi et al., Brain Res., 552:67-76, 1991). MN9D cells synthesize catecholamines, have embryonic properties, express neuron-specific markers, and are sensitive to the DA cell toxin N-methyl-4-phenylpyridinium (MPP) (Kim et al., Biochem. Biophys. Res. Commun., 286:659-665, 2001). In these experiments, MN9D cells are maintained at 37° C., with 5% CO2 in DMEM/F12 medium supplemented with 10% fetal calf serum, 100 U/ml penicillin, and 100 µg/ml streptomycin. Total RNA from MN9D cells exposed to candidate compounds is prepared using TriReagent followed by treatment with Dnase I. cDNA is obtained using 5 µg of RNA with the SuperScript™ first-strand synthesis system for RT-PCR. The resulting cDNA is used as a template for PCR reactions. The following primer sets may be used for real time PCR analyses:

```
                                          (SEQ ID NO: 1)
Actin: 5'-GGCATTGTGATGGACTCCGG-3'
and (SEQ ID NO: 2)
5'-TGCCACAGGATTCCATACCC-3' (358 bp);

(SEQ ID NO: 3)
TH: 5'-TTGGCTGACCGCACATTTG-3'
and (SEQ ID NO: 4)
5'-ACGAGAGGCATAGTTCCTGAGC-3' (336 bp);

(SEQ ID NO: 5)
GAD: 5'-GGGTTTGAGGCACACATTGATAAG-3'
and (SEQ ID NO: 6)
5'-GCGGAAGAAGTTGACCTTGTCC-3' (279 bp);

(SEQ ID NO: 7)
Nurr1: 5'-CATGGACCTCACCAACACTG-3'
and (SEQ ID NO: 8)
5'-GAGACAGGTGTCTTCCTCTG-3' (383 bp).
```

Real-time PCR may be performed in order to quantify expression levels. The amplifications may be performed in 25 µl volumes containing 0.5 µM of each primer, 0.5 X SYBR Green I (Molecular Probes), and 2 µl of 10-fold diluted cDNA using the DNA engine Opticon™ (MJ Research, Waltham, Mass.). The PCR reactions consist of fifty cycles using the following temperature profile: 95° C. for thirty seconds, 60° C. for thirty seconds, 72° C. for thirty seconds, and 79° C. for five seconds. The melting temperature of each PCR product is determined. After each PCR cycle, the fluorescent signals is detected at 79° C. in order to melt primer dimers (the $T_m$, of all primer dimers utilized herein is less than 79° C.). The purity of each PCR product (defined as the presence of a single, specific band) is then confirmed by gel electrophoresis. A standard curve is constructed using GAPDH plasmid DNA (from $10^3$ to $10^8$ molecules). The fluorescent signals from specific PCR products is then normalized against that of actin. For each gene, two independent samples are analyzed, and all of the reactions should be repeated at least twice.

Quantification of dopamine by HPLC. HPLC analyses of dopamine are performed with cell lysate after exposure to candidate compounds. The cell lysates from six wells are pooled and the proteins precipitated by adding 200 µl of perchloric acid (PCA) and EDTA at final concentrations of 0.33 M and 0.17 mM, respectively. After centrifugation at 14,000×g for ten minutes, the intracellular fraction (supernatant) and cell pellet are separated for intracellular DA and protein analysis, respectively. HPLC analysis with electrochemical detection may be performed as described in Andersson et al., Neurotoxicology, 16:201-210, 1995, using a reverse-phase column for separation.

Immunostaining of TH protein. After compound treatment, MN9D cells are fixed with 4% formaldehyde (Electron Microscopy Sciences, Ft. Washington, Pa.) for thirty minutes, rinsed with PBS, and then incubated with blocking buffer [PBS, 10% normal donkey serum (NDS) or normal goat serum (NGS), 0.1% Triton X-100] for ten minutes. Cells are incubated overnight at 4° C. with primary antibodies diluted in PBS containing 2% NDS or NGS. A variety of primary antibodies may be used, e.g., rabbit anti-β-tubulin (1:2000; Covance, Richmond, Calif.), sheep anti-TH (1:200; Pel-Freez, Rogers, Ark.), sheep anti-AADC (1:200; Chemicon, Temecula, Calif.), rat anti-DAT (1:1000; Chemicon), or rabbit anti-5-hydroxytryptamine (HT) (1:3000; Diasorin, Stillwater, Minn.). The proteins are then precipitated using anti-γ-aminobutyric acid (GABA) (1:5000; Sigma). After washing with PBS, the coverslips are incubated with fluorescent-labeled secondary antibodies, e.g., Alexa Fluor 488 (green) or Alexa Fluor 568(red)-labeled donkey/goat IgG (1:500; Molecular Probes, Oreg.), in PBS with 2% NDS or NGS for thirty minutes at room temperature. After rinsing for 3×10 minutes in PBS, the coverslips are then mounted onto slides using Gel/Mount (Biømeda Corp., Foster City, Calif.). Cells may be examined using a Leica TCS/NT confocal microscope equipped with krypton, krypton/argon and helium lasers. Cells may be counted according to the protocol described in Chung et al., Eur. J. Neurosci., 16:1829-1838, 2002, or modified versions thereof.

Example 4

Dopaminergic Neuronal Cell Differentiation

For in vitro differentiation of ES cells, we used the 5-stage method, which is known in the art (see, e.g., Lee et al., Nat. Biotechnol. 18:675-679, 2000) and is useful for distinguishing each stage of developmental progression of ES cells. The mouse blastocyst-derived ES cell lines D3 and J1 were propagated and maintained according to methods well-known in the art (see, e.g., Deacon et al., Exp. Neurol., 149:28-41, 1998, and Chung et al., Stem Cells, 20:139-145, 2002). The mouse ES cells were generated as embryoid bodies (EBs) on nonadherent bacterial dishes for four days in growth medium consisting of DMEM supplemented with 2 mM L-glutamine, 0.001% β-mercaptoethanol, 1× non-essential amino acids (all from Invitrogen), and 10% FBS (Hyclone). The EBs were then plated onto adhesive tissue culture dish surfaces. After 24 hours in culture, selection of nestin-positive cells was performed in serum-free ITSFn medium. After ten days of selection, nestin-positive cells were expanded by dissociating the cells via trypsinization and subsequent plating on poly-L-ornithine/Fibronectine-coated coverslips in N2 medium supplemented with laminin (1 µg/ml) and basic fibroblast growth factor (bFGF) (10 ng/ml) (Invitrogen). Differentiation of the neuronal precursor cells was induced by withdrawing bFGF from N2 medium containing laminin. To see the effect of amodiaquine (4E), we added each 2 uM 4E compound to ES-derived neurons at day five of the ES-derived neuronal stage for a period of four days.

Figure 10A:
FIG. 10A is a pair of photos showing embryonic stem (ES) cell-derived neurons subjected to an indirect immunohistochemical assay (TH+/Tuj1+ staining). ES-derived neurons were immunolabeled with anti-β-tubulin III and anti-TH. Superposition of both proteins under a fluorescent microscope is shown in white. DMSO was used as a control.
Figure 10A:
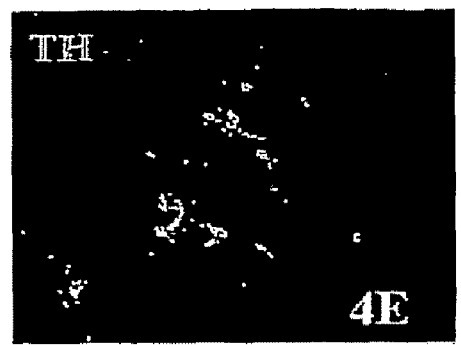
Figure 10B:
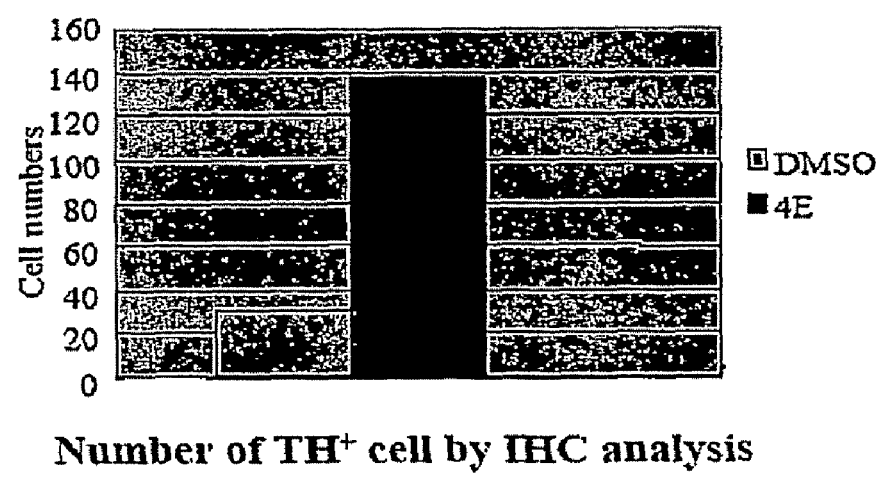
FIG. 10B is a bar graph showing that amodiaquine increased the number of TH+ cells during in vitro ES cell differentiation in comparison with the control, DMSO.

Cells were fixed in four percent paraformaldehyde in 1×PBS, mounted on glass slides, and stained with primary antibodies including anti-TH (Pelfreeze) and anti-β-tubulin 111 (Covance) (FIGS. 10A-10B). Appropriate Alexa488- and Alexa555-labeled secondary antibodies (Molecular Probes) and 4',6-diamidino-2-phenylindole counterstain were used for visualization.

Other Embodiments

All publications, patents, and patent applications mentioned in the above specification are hereby incorporated by reference. Various modifications and variations of the described method and system of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the art are intended to be within the scope of the invention.

Other embodiments are in the claims.

What is claimed is:

1. A method for treating or inhibiting the development of Parkinson's Disease comprising the steps of:
   (a) determining whether a patient has or is at risk of developing Parkinson's Disease; and
   (b) if said patient has or is at risk of developing Parkinson's Disease, administering to said patient a pharmaceutical composition comprising amodiaquine in an amount sufficient to treat or inhibit the development of Parkinson's Disease and a pharmaceutically acceptable excipient.

* * * * *